(12) United States Patent
Kitakawa et al.

(10) Patent No.: US 11,691,940 B2
(45) Date of Patent: Jul. 4, 2023

(54) PRODUCTION METHOD FOR POLYVALENT ALCOHOL ESTER COMPOUNDS

(71) Applicant: TOHOKU UNIVERSITY, Sendai (JP)

(72) Inventors: Naomi Kitakawa, Sendai (JP); Kousuke Hiromori, Sendai (JP); Kazuki Murakami, Sendai (JP); Tomoya Watanabe, Sendai (JP)

(73) Assignee: TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 17/261,211

(22) PCT Filed: Aug. 9, 2019

(86) PCT No.: PCT/JP2019/031714
§ 371 (c)(1),
(2) Date: Jan. 19, 2021

(87) PCT Pub. No.: WO2020/032271
PCT Pub. Date: Feb. 13, 2020

(65) Prior Publication Data
US 2021/0276938 A1    Sep. 9, 2021

(30) Foreign Application Priority Data

Aug. 10, 2018 (JP) ................ 2018-152108

(51) Int. Cl.
*C07C 67/08* (2006.01)
(52) U.S. Cl.
CPC .................. *C07C 67/08* (2013.01)
(58) Field of Classification Search
CPC   C07C 67/08; C07C 69/28; B01J 31/08; B01J 2231/49; B01J 37/0203; C07B 61/00
See application file for complete search history.

(56) References Cited

U.S. PATENT DOCUMENTS

| | | | |
|---|---|---|---|
| 3,669,848 A | 6/1972 | Seiden | |
| 8,501,393 B2 | 8/2013 | Hatanaka et al. | |
| 2007/0202073 A1* | 8/2007 | Fenyvesi | A61K 36/355 424/70.31 |
| 2020/0123094 A1* | 4/2020 | Kitakawa | C07C 67/08 |

FOREIGN PATENT DOCUMENTS

| | | | |
|---|---|---|---|
| EP | 3 205 341 A1 | 8/2017 | |
| JP | 59-172459 A | 9/1984 | |
| JP | 03-044350 A | 2/1991 | |
| JP | 05-246947 A | 9/1993 | |
| JP | 11-193262 A | 7/1999 | |
| JP | 2002 088019 | * | 3/2002 |
| JP | 2002-088019 A | | 3/2002 |
| JP | 2008-037837 A | | 2/2008 |
| JP | 2008-037847 A | | 2/2008 |
| JP | 4509106 B2 | | 7/2010 |
| JP | 2013-159685 A | | 8/2013 |
| JP | 2013159685 | * | 8/2013 |
| JP | 6023358 B2 | | 11/2016 |
| WO | WO2018/230702 | * | 12/2018 |

OTHER PUBLICATIONS

JP2002 088019 Translated (Year: 2002).*
JP2013 159685 Translated (Year: 2013).*
Socratic (two pages) (Year: 2016).*
Adam Macierzanka et al., "Micro structural behavior of water-in-oil emulsions stabilized by fatty acid esters of propylene glycol and zinc fatty acid salts", Colloids and Surfaces A: Physicochemical and Engineering Aspects, 2006, pp. 125-137, vol. 281, Issues 1-3.
Japan's Specifications and Standards for Food Additives, 9th Ed., Ministry of Health, Labour and Welfare, 2018, pp. 894-895.
Elwira Sadecka et al., "One-Step Synthesis of W/O and O/W Emulsifiers in the Presence of Surface Active Agents", Journal of Surfactants and Detergents, May 2013, pp. 305-315, vol. 16.
Pierrick Fevrier et al., "Evaluation of regioselectivity of lipases based on synthesis reaction conducted with propyl alcohol, isopropyl alcohol and propylene glycol", Journal of Molecular Catalysis B: Enzymatic, 2001, pp. 445-453, vol. 11.
International Search Report of PCT/JP2019/031714 dated Oct. 1, 2019 [PCT/ISA/210].
Office Action dated Sep. 28, 2022 in Indonesian Application No. P00202101353.
Office Action dated Dec. 6, 2022 issued by the Japanese Patent Office in corresponding Japanese Application No. 2020-535930.

* cited by examiner

*Primary Examiner* — Yevgeny Valenrod
*Assistant Examiner* — Blaine G Doletski
(74) *Attorney, Agent, or Firm* — Sughrue Mion, PLLC

(57) ABSTRACT

A method for producing a polyvalent alcohol ester compound, characterized in that a polyvalent alcohol compound and a carboxylic acid compound are allowed to react in the presence of an acidic solid catalyst swollen with the polyvalent alcohol compound or the carboxylic acid compound without using a solvent to selectively produce a monocarboxylic acid ester or a polycarboxylic acid ester of a polyvalent alcohol. In this manner, a mono-fatty acid ester and a poly-fatty acid ester (e.g., di-fatty acid ester) of a polyvalent alcohol can be selectively and effectively produced from a polyvalent alcohol compound and a fatty acid compound.

21 Claims, 5 Drawing Sheets

[FIG. 1]
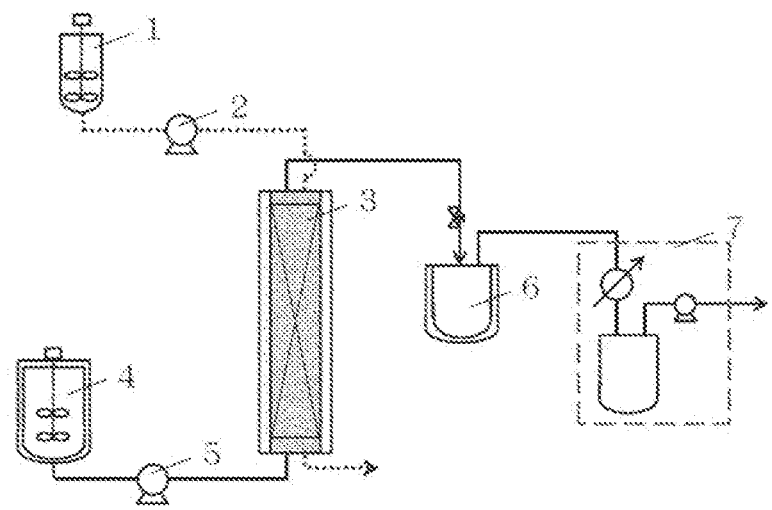
[FIG. 2]
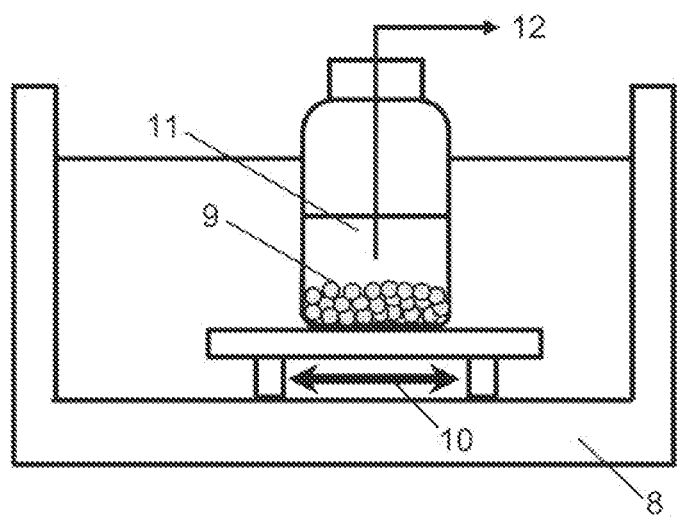

[FIG. 3]
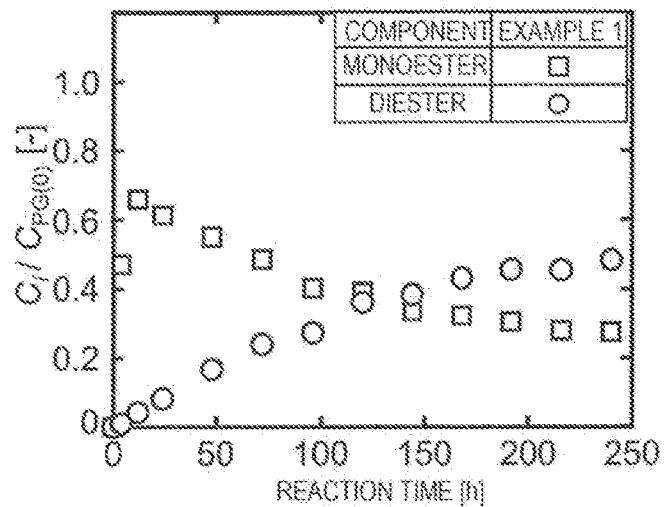
[FIG. 4]
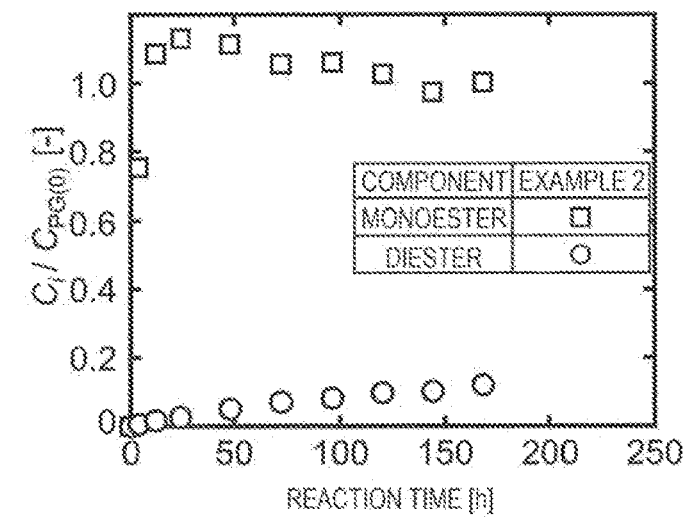
[FIG. 5]
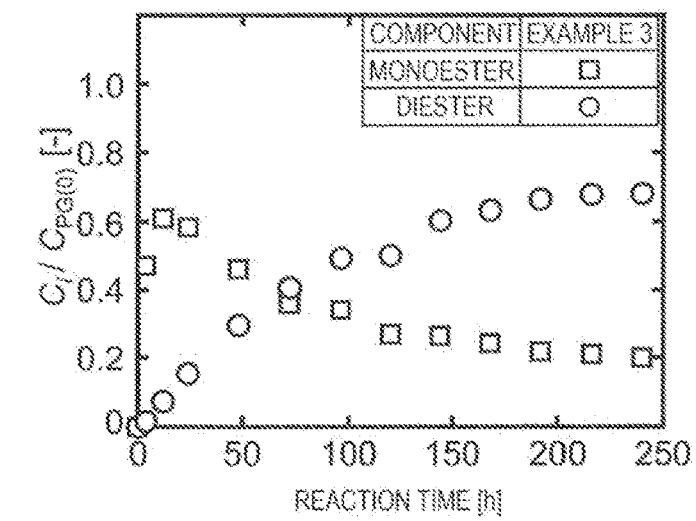

[FIG. 6]
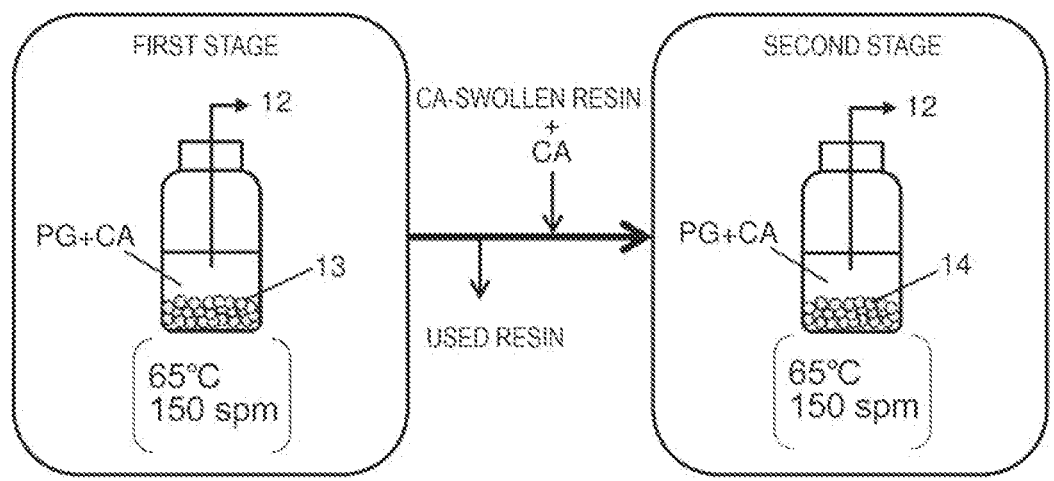
[FIG. 7]
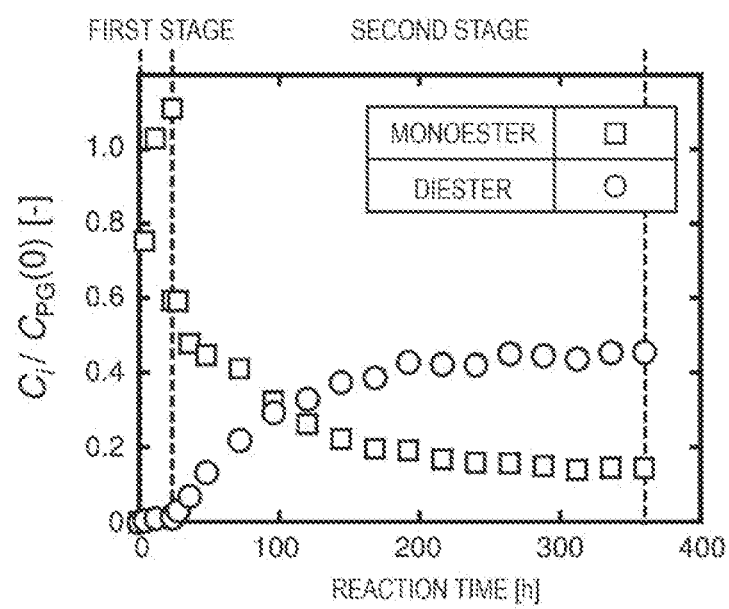

[FIG. 8]
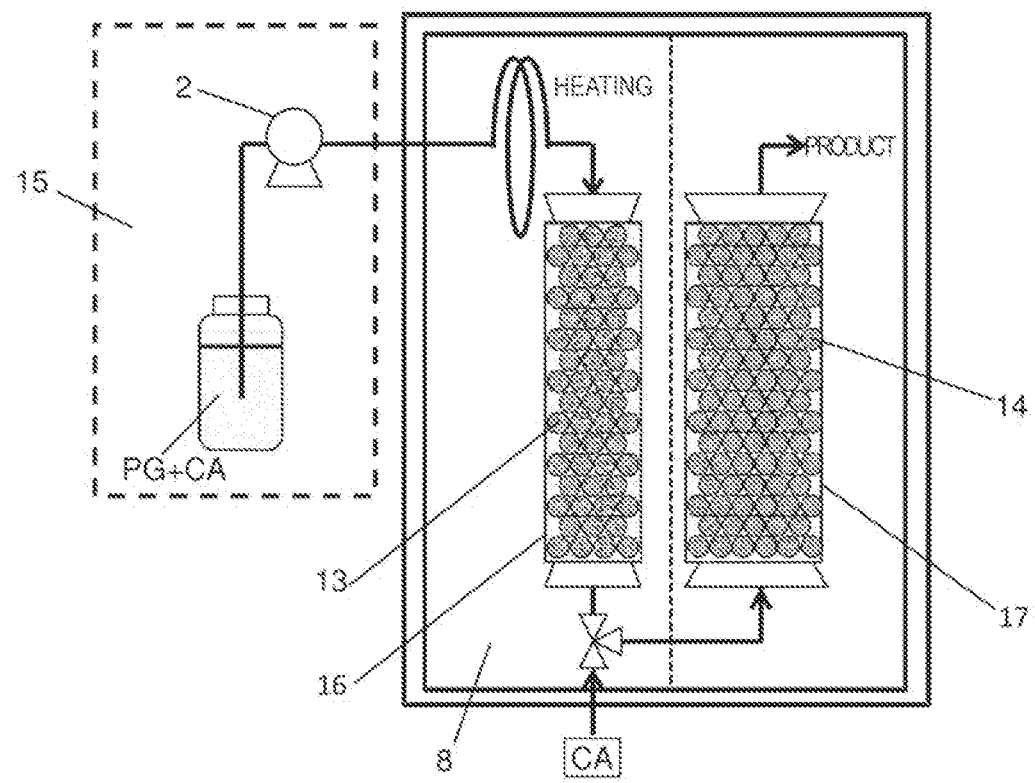
[FIG. 9]
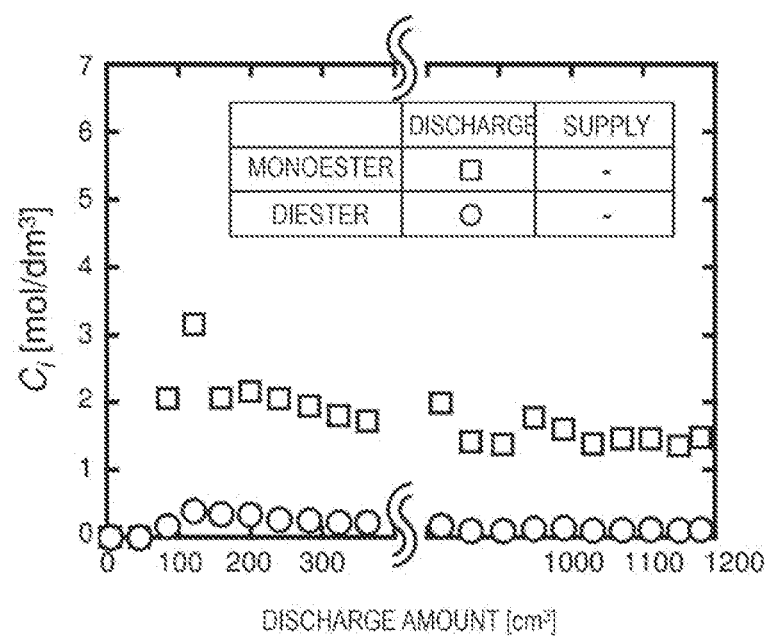

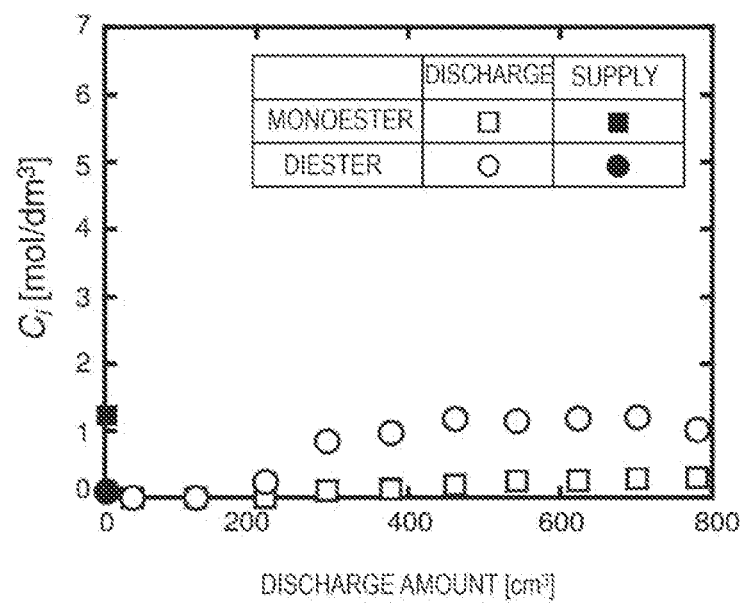
[FIG. 10]

PRODUCTION METHOD FOR POLYVALENT ALCOHOL ESTER COMPOUNDS

CROSS REFERENCE TO RELATED APPLICATIONS

This application is a National Stage of International Application No. PCT/JP2019/031714 filed on Aug. 9, 2019, claiming priority based on Japanese Patent Application No. 2018-152108 filed on Aug. 10, 2018.

TECHNICAL FIELD

The present invention relates to a method for producing a polyvalent alcohol ester compound. More specifically, it relates to a method for selectively producing a mono-fatty acid ester and a poly-fatty acid ester (e.g., di-fatty acid ester) of a polyvalent alcohol from a polyvalent alcohol compound and a fatty acid compound.

BACKGROUND ART

Carboxylic acid compound esters of polyvalent alcohols (sometimes simply referred as "polyvalent alcohol esters"), such as polyvalent esters resulting from a reaction between propylene glycol and a fatty acid, include monoesters and diesters, and monoesters have been used as emulsifiers for foods (NPL 1). In addition, diesters improve the storage stability or solubility of drugs when added in small amounts, and thus have been utilized in preparations for external application and the like (PTLs 1 and 2).

Currently, these esters are produced, using a homogeneous acid catalyst, from a successive esterification reaction using propylene glycol and a fatty acid as raw materials (NPL 2). However, an esterification reaction is a reversible reaction, and, in order to achieve high conversion, high-temperature conditions or reduced-pressure conditions for the removal of by-product water are required (NPL 3 and PTL 3). In addition, under high-temperature conditions, harmful substances, such as glycidol and 3-chloro-1,2-propanediol (3-MCPD), are produced as by-products. Thus, a method for synthesizing a polyvalent alcohol ester under milder conditions has been demanded. In addition, as compared with the synthesis of a monoester, the reaction to synthesize a diester is less likely to proceed, and thus the reaction is carried out under severer conditions. However, it is difficult to selectively obtain only a diester, and it is indispensable to subject a mixture of unreacted components, the monoester form, and the diester form to a separation operation. A separation operation is generally performed by molecular distillation. However, a high-temperature operation is required here too, and thus the by-production of harmful substances described above poses a problem.

With respect to propylene glycol (propane-1,2-diol), because the 1-position and 2-position hydroxyl groups have different reactivities, and the 2-position hydroxyl group has a lower reactivity, the selective synthesis of a diester requires even severer conditions. Thus, a method for selectively synthesizing a diester under milder conditions has been studied.

As catalysts that selectively synthesize a propylene glycol ester, lipase enzymes have been studied in the past (NPL 4). According to NPL 4, the feed molar ratio between propylene glycol and caprylic acid is set at 1:1, and ester synthesis is performed using a lipase immobilized on a silica gel carrier at 40° C. It has been reported that in the case where t-butyl methyl ether is used as a solvent, within 2 hours, the 1-position monoester yield is 65%, the 2-position monoester yield is 5%, and the diester yield is 2%, while in the case where hexane is used as a solvent, within 24 hours, the 1-position monoester yield is 33%, the 2-position monoester yield is 7%, and the diester yield is 38%. It is believed that the difference in behavior among these polyvalent alcohol hydroxyl groups during the reaction is attributable to the polarity difference between the product and the solvent, and that a polar solvent is suitable for the synthesis of monoesters, while a nonpolar solvent is suitable for the synthesis of diesters. However, t-butyl methyl ether has the problem of toxicity and thus, for safety, has to be completely removed by a separation operation upon the utilization of the product, resulting in the problem in that the production cost further increases.

As prior art related to the invention, the present inventors have proposed a method for producing a fatty acid ester from an esterification reaction between a free fatty acid residual oil including 95% or more free fatty acids and a monovalent alcohol, in which a cation exchange resin used as a catalyst is previously swollen with the reaction raw material alcohol (JP-A-2013-159685; PTL 4). PTL 4 uses a monovalent alcohol (and neither describes nor suggests the use of a polyvalent alcohol), and swelling with a carboxylic acid (fatty acid) is nowhere described.

JP-A-59-172459 (PTL 5) discloses a cation exchange resin as an esterification catalyst that can be used in the production of a polyvalent alcohol ester from an esterification reaction between a polyvalent alcohol and a carboxylic acid. However, it is nowhere described that the cation exchange resin is previously swollen with the raw material polyvalent alcohol or carboxylic acid.

Further, JP-A-2008-37847 (PTL 6) also describes a method for producing the mono-form of a polyvalent alcohol ester from a polyvalent alcohol and a carboxylic acid using a strongly acidic cation exchange resin as a catalyst. However, it is nowhere described that the strongly acidic cation exchange resin is previously swollen with the polyvalent alcohol or the carboxylic acid.

CITATION LIST

Patent Literature

PTL 1: Japanese Patent No. 6023358 (EP-A-3205341)
PTL 2: Japanese Patent No. 45.0S1.06 (U.S. Pat. No. 8,501,353)
PTL 3: U.S. Pat. No. 3,669,848
PTL 4: JP-A-2013-159685
PTL 5: JP-A-59-172459
PTL 6: JP-A-2008-37847

Non Patent Literature

NPL 1: Colloid Surf., 281, 125-137 (2006)
NPL 2: Japan's Specifications and Standards for Food Additives, 9$^{th}$ Ed., Ministry of Health, Labour and Welfare, 894-895 (2018)
NPL 3: J. Surf. Deterg., 16, 305-315 (2013)
NPL 4: J. Mol. Catal., 11, 445-453 (2001)

SUMMARY OF INVENTION

Technical Problem

An object of the invention is to overcome the deficiencies of the prior art and provide a method for selectively and effectively producing a mono-fatty acid ester and a poly-fatty acid ester (e.g., di-fatty acid ester) of a polyvalent alcohol from a polyvalent alcohol compound and a fatty acid compound.

Solution to Problem

The present inventors have conducted intensive research. As a result, they have found that when a commercially available cation exchange resin for use in a water treatment, for example, is used as an acidic solid catalyst in a reaction between a polyvalent alcohol compound and a carboxylic acid compound, high-conversion ester synthesis under mild conditions is enabled, and also that, in this case, when, as a pretreatment, the cation exchange resin used as a catalyst is swollen with the reaction raw polyvalent alcohol or carboxylic acid compound, the number of carboxylic acids ester combined with the polyvalent alcohol can be controlled, and a polyvalent alcohol ester compound having bonded thereto a specific number of carboxylic acids can be selectively synthesized, and thus accomplished the invention.

The invention relates to the method for producing a polyvalent alcohol ester compound according to the following [1] to [10].

[1] A method for producing a polyvalent alcohol eater compound, characterized in that a polyvalent alcohol compound and a carboxylic acid compound are allowed to react in the presence of an acidic solid catalyst swollen with the polyvalent alcohol compound or the carboxylic acid compound to selectively produce a monocarboxylic acid ester or a polycarboxylic acid ester of a polyvalent alcohol.

[2] The method for producing a polyvalent alcohol ester compound according to the above item 1, wherein the polyvalent alcohol compound and the carboxylic acid compound are allowed to react without using a solvent.

[3] The method for producing a polyvalent alcohol ester compound according to the above item 1 or 2, wherein the polyvalent alcohol compound is a divalent alcohol.

[4] The method for producing a polyvalent alcohol ester compound according to any one of the above items 1 to 3, wherein the polyvalent alcohol compound is a polyvalent alcohol compound having 2 to 30 carbon atoms.

[5] The method for producing a polyvalent alcohol ester compound according to any one of the above items 1 to 4, wherein the carboxylic acid compound is a fatty acid haying 2 to 30 carbon atoms.

[6] The method for producing a polyvalent alcohol ester compound according to any one of the above items 1 to 5, wherein the acidic solid catalyst is a cation exchanger.

[7] The method for producing a polyvalent alcohol eater compound according to any one of the above items 1 to 6, wherein the polyvalent alcohol and a carboxylic acid compound are allowed to react using, as a catalyst, a cation exchanger previously swollen with the polyvalent alcohol to selectively synthesize a monoester compound.

[8] The method for producing a polyvalent alcohol ester compound according to any one of the above items 1 to 6, wherein the polyvalent alcohol and a carboxylic acid compound are allowed to react using, as a catalyst, a cation exchanger previously swollen with the carboxylic acid compound to selectively synthesize a polyester compound.

[9] The method for producing a polyvalent alcohol ester compound according to the above item 7, wherein propylene glycol and caprylic acid are allowed to react using, as a catalyst, a cation exchanger previously swollen with propylene glycol to selectively synthesize a monoester compound.

[10] The method for producing a polyvalent alcohol ester compound according to the above item 8, wherein propylene glycol and caprylic acid are allowed to react using, as a catalyst, a cation exchanger previously swollen with caprylic acid to selectively synthesize a diester compound.

Advantageous Effects of Invention

According to the ester production method of the invention, in which a polyvalent alcohol and a carboxylic acid are allowed to react using a cation exchanger as an acidic solid catalyst, a monocarboxylic acid ester or a polycarboxylic acid ester can be produced with high selectivity.

According to the method of the invention, (1) as compared with the prior art, an operation under mild conditions is possible, and there is no decrease in the activity of the catalyst due to repeated use. In addition, because a monoester compound and a polyester compound can be selectively synthesized, the separation load is reduced, allowing for production at low cost.

(2) Even an ester compound having a high molecular weight, which conventionally has to be synthesized through a multi-stage process because, in an esterification reaction that is a reversible reaction, as compared with monoesterification, the diester in the subsequent stage is less reactive, can also be produced in a single stage at low cost.

(3) The ester compound produced in the invention forms products for various applications depending on the number of unreacted hydroxyl groups in the polyvalent alcohol molecule that serves as the backbone. For example, in the case where at least one unreacted hydroxyl group is present, such a compound can be utilized as an amphiphilic compound such as an emulsifier or a surfactant, a low-caloric functional oil/fat, or a food additive, while in the case where no unreacted hydroxyl group is present, such a compound can be utilized as a pharmaceutical such as a preparation for external application, a healthy functional oil/fat, an additive for foods, or the like.

(4) In the prior art where a homogeneous acid (phosphoric acid, sulfuric acid, p-toluenesulfonic acid) or the like is used as a catalyst, usually, the catalyst is separated by neutralization/washing. However, because the separation of the catalyst is insufficient in a single operation, the separation operation is repeated several times, or the separation is performed using a complicated technique that combines a plurality of unit operations such as distillation, extraction, and crystallization. In contrast, in the method of the invention using a solid catalyst, the catalyst can be separated merely by a filtration operation. Therefore, production in a continuous flow using a packed reactor as shown in FIG. 1, FIG. 6, and FIG. 8 is possible.

BRIEF DESCRIPTION OF DRAWINGS

FIG. 1 shows the overview of an example of an apparatus for implementing the esterification reaction of the invention in a continuous flow.

FIG. 2 shows the overview of a batch-type reaction apparatus used in Examples 1 to 3.

FIG. 3 is a graph showing time course of the dimensionless concentrations change for a monoester compound and a diester compound, which are products of an esterification reaction between propylene glycol (PG) and caprylic acid (CA) (Example 1).

FIG. 4 is a graph showing time course of the dimensionless concentrations change for a monoester compound and a diester compound in the esterification reaction of Example 2.

FIG. 5 is a graph showing time course of the dimensionless concentrations change for a monoester compound and a diester compound in the esterification reaction of Example 3.

FIG. 6 shows the overview of the apparatus used in the two-stage esterification reaction of Example 4.

FIG. 7 is a graph showing time course of the dimensionless concentrations change for a monoester compound and a diester compound in the esterification reaction of Example 4.

FIG. 8 shows the overview of the apparatus used in the two-stage esterification reaction of Example 5 using catalyst-packed columns connected in series.

FIG. 9 is a graph showing time course of the dimensionless concentrations change for a monoester compound and a diester compound in the esterification reaction in the first stage of Example 5.

FIG. 10 is a graph showing time course of the dimensionless concentrations change for a monoester compound and a diester compound in the esterification reaction in the second stage of Example 5.

DESCRIPTION OF EMBODIMENTS

The method for producing a polyvalent alcohol ester compound of the invention is characterized in that a polyvalent alcohol compound and a carboxylic acid compound are allowed to react in the presence of an acidic solid catalyst (cation exchanger) preferably without using a solvent, thereby selectively producing a monocarboxylic acid ester or a polycarboxylic acid ester (e.g., dicarboxylic acid ester) of a polyvalent alcohol.

Incidentally, as used herein, to "selectively produce" means to produce an ester compound having an arbitrary number of hydroxyl groups with a selectivity of 50 mol % or more.

As the polyvalent alcohol compound, a polyvalent alcohol having 2 to 30 carbon atoms is used. The polyvalent alcohol may have an ether bond, a carbon-carbon double bond, a carbon-carbon triple bond, an aromatic ring, or an alicyclic structure at an arbitrary position in the carbon chain. Examples of such polyvalent alcohols include ethylene glycol, glycerin, 1,3-propanediol, propylene glycol (1,3-propanediol), 1,2-butanediol, 1,3-butanediol, 1,4-butanediol, and 2,3-butanediol. Among them, ethylene glycol, 1,3-propanediol, propylene glycol, 1,2-butanediol, 1,3-butanediol, 1,4-butanediol, and 2,3-butanediol, which are divalent alcohols, are preferable, for example. In addition, as used herein, polyvalent alcohols also include polymer compounds having a diol-terminated structure resulting from the polymerization of ethylene glycol.

As the carboxylic acid compound, a fatty acid having 2 to 30 carbon atoms is used. Fatty acids having 10 to 24 carbon atoms are preferable, and fatty acids having 14 to 20 carbon atoms are still more preferable.

The carboxylic acid compound may also have an ether bond, a carbon-carbon double bond, a carbon-carbon triple bond, an aromatic ring, or an alicyclic structure at an arbitrary position in the carbon chain. Examples of carboxylic acid compounds include caproic acid, enanthic acid, heptanoic acid, caprylic acid, pelargonic acid, capric acid, lauric acid, myristic acid, stearic acid, palmitic acid, oleic acid, linoleic acid, linoienic acid, arachidic acid, and behenic acid. Among them, myristic acid, palmitic acid, stearic acid, and arachidic acid are particularly preferable.

In the invention, as a solid catalyst, a known porous strongly acidic cation exchanger (sometimes referred to as "cation exchanger" or "strongly acidic cation exchanger") is used.

The form of the cation exchanger is not particularly limited, and may be granular, membranous, fibrous, or the like. As cation exchanger-forming resins, those whose resin backbones have various chemical structures as insoluble carriers can be used. Specific examples thereof include synthetic polymers, such as polystyrene crosslinked with divinylbenzene or the like, polyacrylic acid, crosslinked poly(meth)acrylic ester, and phenol resin, and crosslinks of naturally occurring polysaccharides, such as cellulose. Among them, synthetic polymers are preferable, and crosslinked polystyrene is still more preferable. The extent (degree) of crosslinking is affected by the amount of divinylbenzene used relative to the total amount of the monomer, and is selected from a range of 1 to 30 mass %, for example. In this case, with a decrease in the degree of crosslinking, a reactant with a greater molecular size is likely to diffuse inside, but the functional group concentration decreases. Thus, for the development of high catalytic activity in an esterification reaction, an optimal value exists.

In the invention, the kind of cation exchange resin used is not particularly limited, and examples thereof include DIAION (registered trademark) PK series (manufactured by Mitsubishi Chemical Corporation), DIAION SK series (same as above), RCP160M (same as above), Amberlite series (manufactured by Dow Chemical Company), and Amberlyst series (same as above). They have a styrene-divinylbenzene copolymer backbone, and the exchange group is a sulfonic acid group. PK208LH, PK212LH, and PK216LH have a porous-type structure, SK104H has a gel-type structure, and RCP160M has a highly porous-type structure. The gel type is a crosslinked polymer that is uniform inside the particle. The porous type is a resin having a structure in which physical holes (pores) are formed in a gel-type resin. The highly porous type is a resin having a structure with a high degree of crosslinking, in which the specific surface area or pore volume is greater than that of the porous type.

As the strongly acidic cation exchange resin, in addition to the sulfonic acid group type, a resin containing a carboxyl group is also applicable.

In a porous strongly acidic resin catalyst, functional groups of the resin are, in any resin, in the catalytically active $H^+$ form ($\geq$99 mol %) at the time of factory shipment, and the catalyst is in a water-swollen state at the time of purchase. Therefore, it is preferable to perform, as a pretreatment, a treatment in which the catalyst is brought into a swollen state with a reactant. This pretreatment is performed as follows: in accordance with the technique proposed by the present inventors (Fuel., 139, 11-17 (2015)), a glass column having an inner diameter of 11 mm (Kiriyame Glass Work Co., Tokyo, ILC-C-11) is packed with a resin, and a polyvalent alcohol or a carboxylic acid is passed through the column at 2.5 $cm^3$/min until the content of the swelling component in the eluate reaches 95 (80) mass % or more.

The present inventors have applied the swelling, which is a pretreatment for functional groups in the porous strongly acidic resin catalyst, also to a carboxylic acid compound, which is the other reaction raw material. As a result, it has turned out that the selectivity of the product (monoester compound or diester compound) significantly differs between the case where the swelling compound is a polyvalent alcohol (propylene glycol) and the case where it is a carboxylic acid compound (caprylic acid), and that swelling with caprylic acid results in the selective production of a diester compound, while swelling with propylene glycol results in the selective production of a monoester compound (see Examples 1 to 3).

Swelling means that the liquid contained in a cation exchanger is brought into contact with a reactant or a solvent to make a filled state. When the swelling liquid contained in the eluate reaches 80 mass % or more, preferably 90 mass %, and more preferably 95 mass %, such a state is referred to as a swollen state. The contact may be made in any style known to those skilled in the art, such as a batch method (batch system) or a continuous method (distribution system). As the form of the apparatus, one equipped with a treatment tank, one in which the resin is transferred through a circulation system or a countercurrent system, and the like can be mentioned. As the contact method, distribution (method in which the liquid is passed through a packed bed of a cation exchange resin), stirring (method in which a stirring tank is used), fluidization (fluidized-bed reactor), shaking (shaking-type reactor), and the like can be mentioned. It is also possible to use a column pass-through type, in which the introduction port for a raw material to be supplied and the recovery port for a product are fixed, or an expanded bed (expanded bed column), and a batch type can also be used.

The molar ratio between the polyvalent alcohol compound and the carboxylic acid compound for use in the esterification reaction of the invention may be 10:1 to 1:10. The molar ratio is more preferably 2:1 to 1:8, and still more preferably 1:1 to 1:6.

A porous strongly acidic resin catalyst can be used through repeated operations of esterification synthesis reactions and resin regeneration treatments. That is, the resin can be reused. For example, the resin after an esterification experiment is recovered by filtration, and, similarly to the pretreatment at the time of purchase, the resin is packed into a column, and a polyvalent alcohol or a carboxylic acid, which is a reactant, is passed through the column, whereby the resin can be washed and regenerated. As a result, the reactants or products remaining inside the resin or on the resin surface can be removed.

[Continuous Flow-Type Esterification Reaction Packed with Porous Strongly Acidic Resin Catalyst]

In the invention, an esterification reaction between a carboxylic acid compound and a polyvalent alcohol compound can be carried out while allowing them to flow through a continuous flow-type catalyst phase packed with a porous strongly acidic resin catalyst. FIG. 1 shows the overview of an example of an apparatus for implementing the process of a continuous flow-type esterification reaction. In the figure, 1 is a raw material polyvalent alcohol tank, 2 is a supply pump, 3 is a reactor (esterification column), 4 is a raw material carboxylic acid tank, 5 is a supply pump, 6 is a product tank, and 7 is an unreacted component separator.

Though a continuous flow-type column packed with a porous strongly acidic resin catalyst, a homogeneous mixture of a carboxylic acid compound and a polyvalent alcohol compound is passed at a predetermined temperature. As a result, the reaction operation can be implemented easily and quickly. The pass-through rate of the reaction mixture in the resin layer is preferably about 0.1 to 100 ml/min per liter resin, for example. In the case where the pass-through rate is less than 0.1 ml/min per liter resin, although the esterification rate improves, the productivity decreases. In addition, in the case where the pass-through rate is more than 100 ml/min per liter resin, the reaction between the reaction mixture and the catalyst is inhibited, and a decrease in ester yield after the reaction may be caused.

In this method for producing a polyvalent alcohol ester compound using a continuous flow-type column, without using other solvents besides the reaction mixture, the kind of polyvalent alcohol compound to react, its feed amount, and the reaction temperature are adjusted, whereby the reaction mixture is brought into a homogeneous state and allowed to react. In the invention, a solvent that does not inhibit the esterification reaction may be used as a column mobile phase as appropriate.

In the esterification reaction of the invention, the contact between the reactant and the strongly acidic resin catalyst can be made by a batch method (batch system) or a continuous flow method (distribution system). As the form of the apparatus, one equipped with a treatment tank, one in which the resin is transferred through a circulation system or a countercurrent system, and the like can be mentioned. As the contact method, distribution (method in which the liquid is passed through a packed bed of a cation exchange resin), stirring (method in which a stirring tank is used), fluidization (fluidized-bed reactor), shaking (shaking-type reactor), and the like can be mentioned. It is also possible to use a column pass-through type, in which the introduction port for a raw material to be supplied and the recovery port for a product are fixed, an expanded bed (expanded bed column), a batch type, or the like.

[Reuse of Acidic Solid Catalyst]

In the invention, when the operations of ester synthesis and acidic solid catalyst reproduction are repeatedly performed, the catalyst can be reused. For example, the resin after a batch-type esterification experiment is recovered by filtration, and, similarly to the pretreatment, the resin is packed into a column, and a polyvalent alcohol or a carboxylic acid, which is a reactant, is passed through the column, whereby the resin can be washed and regenerated. As a result, the reactants or products remaining inside or on the surface of the resin can be removed.

EXAMPLES

Hereinafter, the invention will be described in detail with reference to examples, but is not limited to the descriptions in the following examples. In the following examples, propylene glycol (PG) (manufactured by Wako Pure Chemical Industries) was used as a raw material polyvalent alcohol, and caprylic acid (CA) (manufactured by Wako Pure Chemical Industries) was used as a fatty acid. In addition, as an acidic solid catalyst, a cation exchange resin (DIAION (registered trademark) PK208LH; manufactured by Mitsubishi Chemical Corporation) was used.

Monoester and Diester Measurement

The propylene glycol-monocaprate (abbreviated to monoester) and propylene glycol-dicaprate (abbreviated to diester) contents in the reaction liquid were measured by a gas chromatograph equipped with a flame ionization detector.

Swelling of Cation Exchange Resin

The cation exchange resin was swollen with PG and CA as follows.

This pretreatment can be performed as follows: in accordance with the technique proposed by the present inventors (Fuel., 139, 11-17 (2015)), a glass column having an inner diameter of 11 mm (Kiriyame Glass Work Co., Tokyo, TLC-C-11) is packed with a resin, and a polyvalent alcohol or a carboxylic acid is passed through the column at 2.5 cm³/min until the content of the swelling component in the eluate reaches 80 mass % or more, preferably 90 mass % or more, and still more preferably 95 mass % or more.

Example 1

An ester synthesis experiment was performed using a batch-type reactor whose overview is shown in FIG. 2. The experimental procedure is as follows. First, the raw materials propylene glycol (PG) and caprylic acid (CA) were added to the reactor (glass bottle) in a molar ratio of 1:2 and preheated in a constant-temperature bath 8 at 65° C. Subsequently, an acidic solid catalyst 9 swollen with CA (DIAION PK208LH, manufactured by Mitsubishi Chemical Corporation) was preheated in the same manner, and an amount that makes 33 mass % of the total reaction liquid (reaction raw materials+resin) was added to the mixture of propylene glycol (PG) and caprylic acid (CA) and allowed to react at 65° C. and 150 spm with shaking 10. A reaction liquid 11 was sampled over time (12) to measure the monoester and diester contents in the reaction liquid. FIG. 3 shows time course of the dimensionless concentrations for the monoester and diester contents in the reaction liquid. The reaction conditions are shown in Table 1, and the results after 240 hours of reaction are shown in Table 2. In FIG. 3, the vertical axis shows the monoester (□) and diester (○) concentrations ($C_i$) relative to the initial concentration of PG ($C_{PG(0)}$) (the same applies to FIG. 4 and FIG. 5).

Selectivity shown in Table 2 was determined by the following equation.

Selectivity (mol %)={(monoester or diester production/amount of propylene glycol that reacted)}×100

Example 2

In the same manner as in Example 1, the raw materials propylene glycol (PG) and caprylic acid (CA) were added to a reactor (glass bottle) in a molar ratio of 1:2 and preheated in the constant-temperature bath 8 at 65° C. Then, the acidic solid catalyst 9 swollen with PG was preheated in the same manner, and an amount that makes 33 mass % of the total reaction liquid (reaction raw materials+resin) was added to the mixture of propylene glycol (PG) and caprylic acid (CA) and allowed to react at 65° C. and 150 spm with shaking. The reaction liquid 11 was sampled over time (12) to measure the monoester and diester contents in the reaction liquid. FIG. 4 shows time course of the dimensionless concentrations for the monoester and diester contents in the reaction liquid. The reaction conditions are shown in Table 1, and the results after 24 hours of reaction are shown in Table 2.

Example 3

The reaction was carried out in the same manner as in Example 1, except that the raw materials propylene glycol (PG) and caprylic acid (CA) were added to a reactor (glass bottle) in a molar ratio of 1:4. The reaction liquid was sampled over time to measure the monoester and diester contents. FIG. 5 shows time course of the dimensionless concentrations for the monoester and diester contents in the reaction liquid. The reaction conditions are shown in Table 1, and the results after 240 hours of reaction are shown in Table 2.

[Table 1]

TABLE 1

| Reaction Conditions | | | |
|---|---|---|---|
| | Example 1 | Example 2 | Example 3 |
| Resin Swelling Liquid | CA | PG | CA |
| PG:CA (Molar Ratio) | 1:2 | 1:2 | 1:4 |
| PG [g] | 3.81 | 3.81 | 3.81 |
| CA [g] | 14.5 | 14.5 | 28.9 |
| Resin Concentration [mass %] | 33 | 33 | 33 |

[Table 2]

TABLE 2

| Experiment Result | | | |
|---|---|---|---|
| | Example 1 | Example 2 | Example 3 |
| Reaction Time (h) | 240 | 24 | 240 |
| Monoester Content (mol/L) | 0.637 | 2.80 | 0.227 |
| Diester Content (mol/L) | 1.11 | 0.072 | 0.781 |
| Selectivity (%) | | | |
| Monoester | 36.4 | 97.5 | 22.2 |
| Diester | 63.5 | 2.5 | 77.5 |

In Example 2 where the reaction was carried out at PG:CA=1:2 using a cation exchange resin previously swollen with PG as a catalyst, after 24 hours of reaction, a monoester was obtained with a selectivity of 97.5 mol %. Meanwhile, in the case of using a cation exchange resin previously swollen with CA as a catalyst, Example 1 where the reaction was carried out at PG:CA=1:2 resulted in a diester selectivity of 63.5 mol % after 240 hours of reaction, while Example 3 where the reaction was carried out at PG:CA=1:4 resulted in a diester selectivity of 77.5 mol % monoester after 240 hours of reaction.

Example 4

In a batch system, a two-stage esterification reaction was carried out using two resins with different swollen states. That is, as shown in FIG. 6, a batch reaction was carried out in the same manner as in Example 1 using a PG-swollen resin (13) in the first stage (Stage 1). Subsequently, the PG-swollen resin (13) was removed, a CA-swollen resin and two mole equivalents of CA were added, and an esterification reaction in the second stage (Stage 2) was carried out. The results are shown in FIG. 7. In FIG. 7, the horizontal axis is the accumulated time from the start of the first stage, and the vertical axis is the dimensionless concentration as in FIG. 1 to 3. In the first stage, almost the entire mixture was converted into a monoester compound within 24 hours. In the second stage, the monoester compound concentration quickly decreased, and, with the decrease, the diester compound concentration increased, indicating that the monoester form was converted into the diester form. These results showed that when resins having different swelled states are used in several stages, the esterification reaction can be controlled.

Example 5

A diesterification reaction was carried out through a two-step process, in which columns packed with a PG-swelled resin and a CA-swelled resin, respectively, were connected in series. The overview of the apparatus is shown in FIG. 8. This apparatus includes a reaction liquid (PG+CA) supply section (15), two column-type reactors (16,17), and the constant-temperature bath (8). In the first stage (Stage 1), 83 g of the same PG-swelled resin as in the batch system of Example 4 was packed into the column (16), maintained at 65° C., and swollen with PG. From the column top part, raw materials were supplied in a stoichiometric molar ratio (1:2) and allowed to react.

In the second stage (Stage 2), the CA-swollen column (17) having the resin in five times the amount in the first stage was used, and the reaction temperature was set at 85° C. To the eluate of the first stage, CA at two times the stoichiometric ratio was supplied from the column bottom part. The column eluate was recovered at predetermined time intervals, and measured and analyzed by GC-FID. The reaction conditions are shown in Table 3, and the results are shown in FIG. 9 and FIG. 10.
[Table 8]

TABLE 3

| Reaction Conditions | | |
|---|---|---|
| | Stage 1 | Stage 2 |
| Resin Swelling Liquid | PG | CA |
| Resin Amount (g-wet) | 83 | 427 |
| Temperature (° C.) | 65 | 85 |
| PG:CA (Molar Ratio) | 1:2 | (1:4) |
| Flow rate (cm$^3$/h) | 1.7 | 1.7 |

In the first stage (see FIG. 9), the monoester compound concentration increased immediately after the start of raw material supply and became constant. Diester compound production was negligible. The proportion of the mono-form in the produced ester after reaching the steady state was 90%, that is, a monoester compound was selectively obtained. The eluate after reaching the steady state was used for the diesterification reaction in the second stage. In the second step (see FIG. 10), the diester compound concentration increased immediately at the start of raw material supply and became constant, and a diester compound was selectively obtained at 83%. That is, through a two-stage reaction using a column with two kinds of resins in different swollen states, it was possible to selectively and continuously synthesize a diester compound.

REFERENCE SIGNS LIST

1: Raw material alcohol tank
2: Supply pump
3: Reactor (esterification column)
4: Raw material carboxylic acid tank
5: Supply pump
6: Product tank
7: Unreacted component separator
8: Constant-temperature bath
9: Acidic solid catalyst
10: Shaking
11: Reaction liquid
12: Sampling
13: PG-swollen resin
14: CA-swollen resin
15: Reaction liquid supply section
16,17: Column-type reactor

The invention claimed is:

1. A method for producing a polyvalent alcohol ester compound, characterized in that a polyvalent alcohol compound and a carboxylic acid compound are allowed to react in the presence of an acidic solid catalyst swollen with the polyvalent alcohol compound to selectively produce a monocarboxylic acid ester of a polyvalent alcohol.

2. The method for producing a polyvalent alcohol ester compound according to claim 1, wherein the polyvalent alcohol compound and the carboxylic acid compound are allowed to react without using a solvent.

3. The method for producing a polyvalent alcohol ester compound according to claim 1, wherein the polyvalent alcohol compound is a divalent alcohol.

4. The method for producing a polyvalent alcohol ester compound according to claim 1, wherein the polyvalent alcohol compound is a polyvalent alcohol compound having 2 to 30 carbon atoms.

5. The method for producing a polyvalent alcohol ester compound according to claim 1, wherein the carboxylic acid compound is a fatty acid having 2 to 30 carbon atoms.

6. The method for producing a polyvalent alcohol ester compound according to claim 1, wherein the acidic solid catalyst is a cation exchanger.

7. The method for producing a polyvalent alcohol ester compound according to claim 1, wherein the polyvalent alcohol and a carboxylic acid compound are allowed to react using, as a catalyst, a cation exchanger previously swollen with the polyvalent alcohol to selectively produce a monoester compound.

8. The method for producing a polyvalent alcohol ester compound according to claim 7, wherein propylene glycol and caprylic acid are allowed to react using, as a catalyst, a cation exchanger previously swollen with propylene glycol to selectively produce a monoester compound.

9. A method for producing a polyvalent alcohol ester compound, characterized in that a polyvalent alcohol compound and a carboxylic acid compound are allowed to react in a first stage in the presence of a first acidic solid catalyst previously swollen with the polyvalent alcohol compound and the product of the first stage is then allowed to react in a second stage in the presence of a second acidic solid catalyst previously swollen with the carboxylic acid compound to selectively produce a polycarboxylic acid ester of a polyvalent alcohol.

10. The method for producing a polyvalent alcohol ester compound according to claim 9, wherein the polyvalent alcohol compound and the carboxylic acid compound are allowed to react without using a solvent.

11. The method for producing a polyvalent alcohol ester compound according to claim 9, wherein the polyvalent alcohol compound is a polyvalent alcohol compound having 2 to 30 carbon atoms.

12. The method for producing a polyvalent alcohol ester compound according to claim 9, wherein the carboxylic acid compound is a fatty acid having 2 to 30 carbon atoms.

13. The method for producing a polyvalent alcohol ester compound according to claim 9, wherein the acidic solid catalyst is a cation exchanger.

14. A method for producing a polyvalent alcohol ester compound, characterized in that a polyvalent alcohol compound and a carboxylic acid compound are allowed to react in the presence of an acidic solid catalyst swollen with the carboxylic acid compound to selectively produce a polycarboxylic acid ester of a polyvalent alcohol.

15. The method for producing a polyvalent alcohol ester compound according to claim 14, wherein the polyvalent alcohol compound and the carboxylic acid compound are allowed to react without using a solvent.

16. The method for producing a polyvalent alcohol ester compound according to claim 14, wherein the polyvalent alcohol compound is a divalent alcohol.

17. The method for producing a polyvalent alcohol ester compound according to claim 14, wherein the polyvalent alcohol compound is a polyvalent alcohol compound having 2 to 30 carbon atoms.

18. The method for producing a polyvalent alcohol ester compound according to claim 14, wherein the carboxylic acid compound is a fatty acid having 2 to 30 carbon atoms.

19. The method for producing a polyvalent alcohol ester compound according to claim 14, wherein the acidic solid catalyst is a cation exchanger.

20. The method for producing a polyvalent alcohol ester compound according to claim 14, wherein the polyvalent alcohol and a carboxylic acid compound are allowed to react using, as a catalyst, a cation exchanger previously swollen with the carboxylic acid compound to selectively produce a polyester compound.

21. The method for producing a polyvalent alcohol ester compound according to claim 20, wherein propylene glycol and caprylic acid are allowed to react using, as a catalyst, a cation exchanger previously swollen with caprylic acid to selectively produce a diester compound.

* * * * *